United States Patent
Fujii

(10) Patent No.: US 11,151,697 B2
(45) Date of Patent: Oct. 19, 2021

(54) ULTRASONIC DIAGNOSIS DEVICE AND PROGRAM

(71) Applicant: Hitachi, Ltd., Tokyo (JP)

(72) Inventor: Nobuhiko Fujii, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 241 days.

(21) Appl. No.: 16/335,835

(22) PCT Filed: Nov. 10, 2017

(86) PCT No.: PCT/JP2017/040622
§ 371 (c)(1),
(2) Date: Mar. 22, 2019

(87) PCT Pub. No.: WO2018/168066
PCT Pub. Date: Sep. 20, 2018

(65) Prior Publication Data
US 2020/0027199 A1 Jan. 23, 2020

(30) Foreign Application Priority Data

Mar. 17, 2017 (JP) .............................. JP2017-052570

(51) Int. Cl.
*G06T 5/00* (2006.01)
*A61B 8/08* (2006.01)

(52) U.S. Cl.
CPC ............ *G06T 5/003* (2013.01); *A61B 8/5207* (2013.01); *A61B 8/5253* (2013.01); *G06T 2207/10132* (2013.01); *G06T 2207/20192* (2013.01)

(58) Field of Classification Search
None
See application file for complete search history.

(56) References Cited

U.S. PATENT DOCUMENTS

| 2006/0084869 | A1 | 4/2006 | Kim et al. |
| 2008/0146931 | A1 | 6/2008 | Zhang et al. |
| 2009/0088638 | A1* | 4/2009 | Sato ........................ A61B 8/13 600/443 |
| 2011/0040183 | A1 | 2/2011 | Yoshida |
| 2012/0041312 | A1 | 2/2012 | Nakahira et al. |

(Continued)

FOREIGN PATENT DOCUMENTS

| CN | 1496715 A | 5/2004 |
| CN | 101199430 A | 6/2008 |

(Continued)

OTHER PUBLICATIONS

International Search Report (PCT/ISA/210) issued in PCT Application No. PCT/JP2017/040622 dated Feb. 13, 2018 with English translation (three (3) pages).

(Continued)

*Primary Examiner* — David Perlman
(74) *Attorney, Agent, or Firm* — Crowell & Moring LLP

(57) ABSTRACT

A basic image generation unit generates a base frame by synthesizing a reception frame sequence obtained by transmission/reception of ultrasonic waves, and an edge-enhanced image generation unit generates a compensation frame where an edge component of an object is emphasized based on the reception frame sequence. A synthesis unit generates an output frame by synthesizing the base frame and the compensation frame.

7 Claims, 9 Drawing Sheets

(56) References Cited

U.S. PATENT DOCUMENTS

| | | |
|---|---|---|
| 2012/0157850 A1 | 6/2012 | Sumi et al. |
| 2015/0018681 A1 | 1/2015 | Nishihara et al. |
| 2015/0196278 A1 | 7/2015 | Noguchi |
| 2018/0092626 A1* | 4/2018 | Waechter-Stehle .......... G01S 7/52079 |

FOREIGN PATENT DOCUMENTS

| | | |
|---|---|---|
| CN | 101396287 A | 4/2009 |
| CN | 101617946 A | 1/2010 |
| CN | 102487603 A | 6/2012 |
| CN | 104783835 A | 7/2015 |
| JP | 2006-116307 A | 5/2006 |
| JP | 2011-56249 A | 3/2011 |
| JP | 2015-33569 A | 2/2015 |
| WO | WO 2010/125789 A1 | 11/2010 |
| WO | WO 2016/198413 A1 | 12/2016 |

OTHER PUBLICATIONS

Japanese-language Written Opinion (PCT/ISA/237) issued in PCT Application No. PCT/JP2017/040622 dated Feb. 13, 2018 (five(5) pages).

Chinese-language Office Action issued in Chinese Application No. 201780071221.X dated May 7, 2021 with English translation (15 pages).

Chinese-language Office Action issued in Chinese Application No. 201780071221.X dated Aug. 16, 2021 (9 pages).

\* cited by examiner

[FIG. 1]
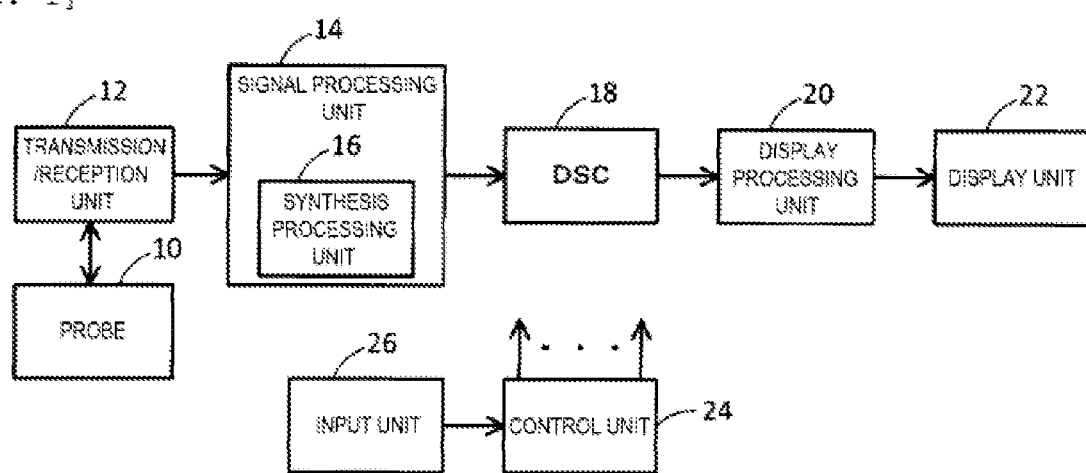

[FIG. 2]
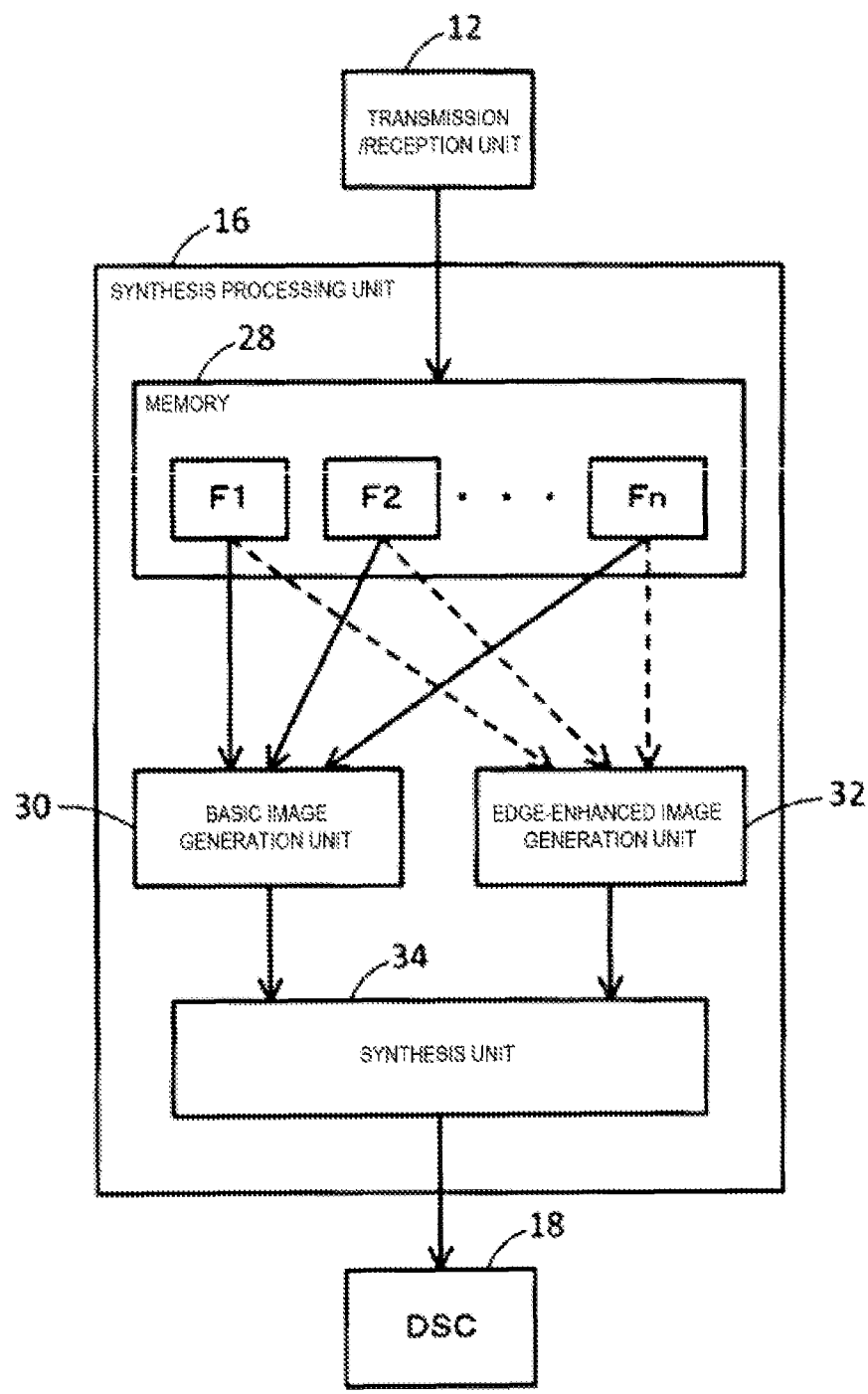

[FIG. 3]
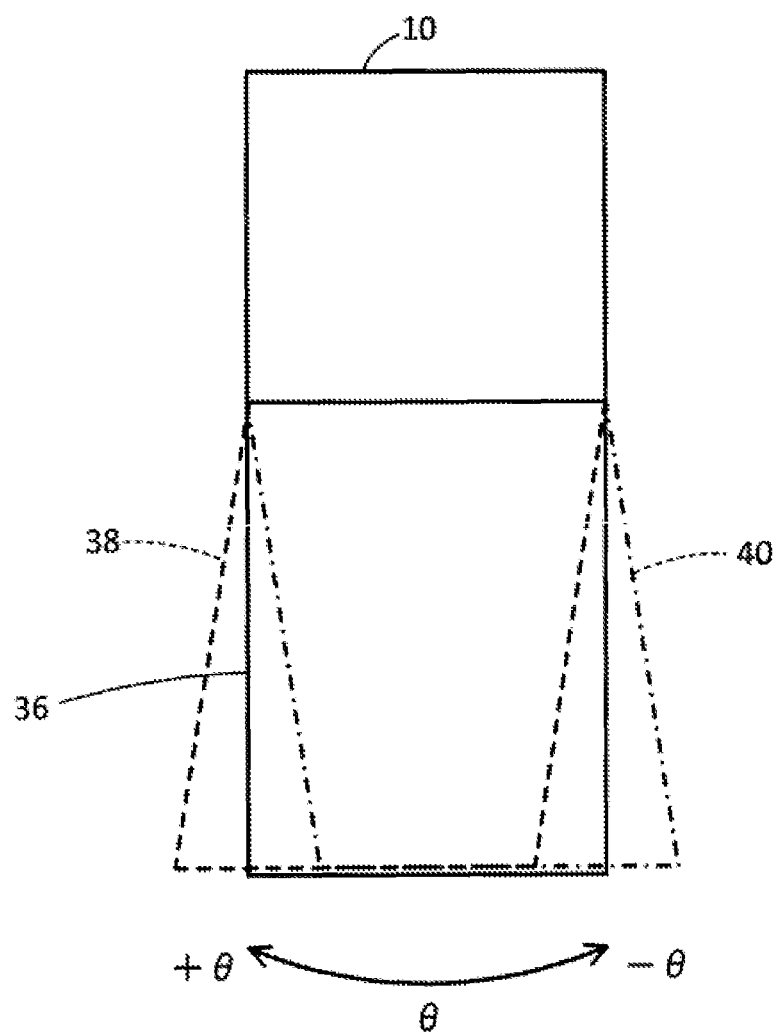

[FIG. 4]
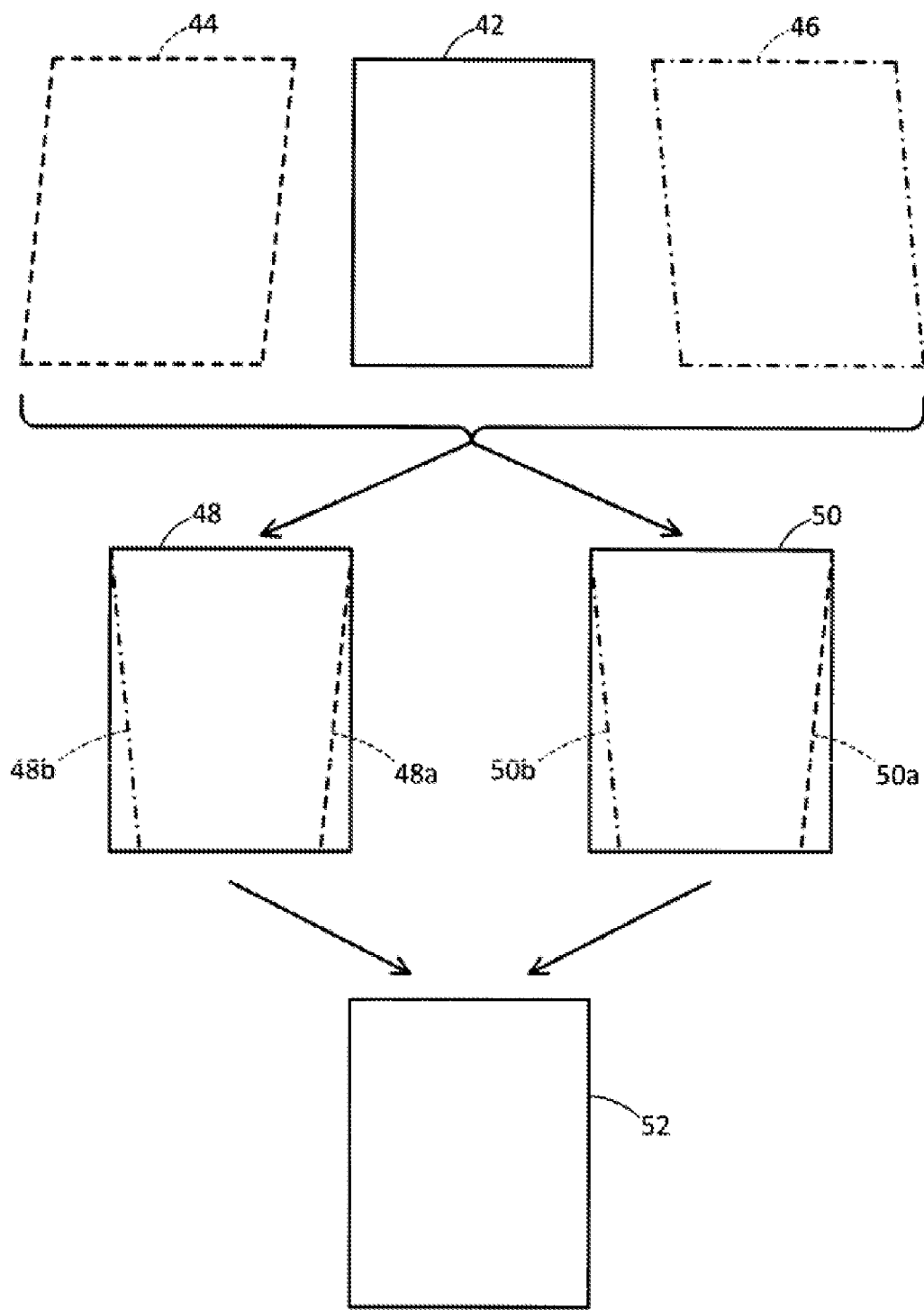

[FIG. 5]
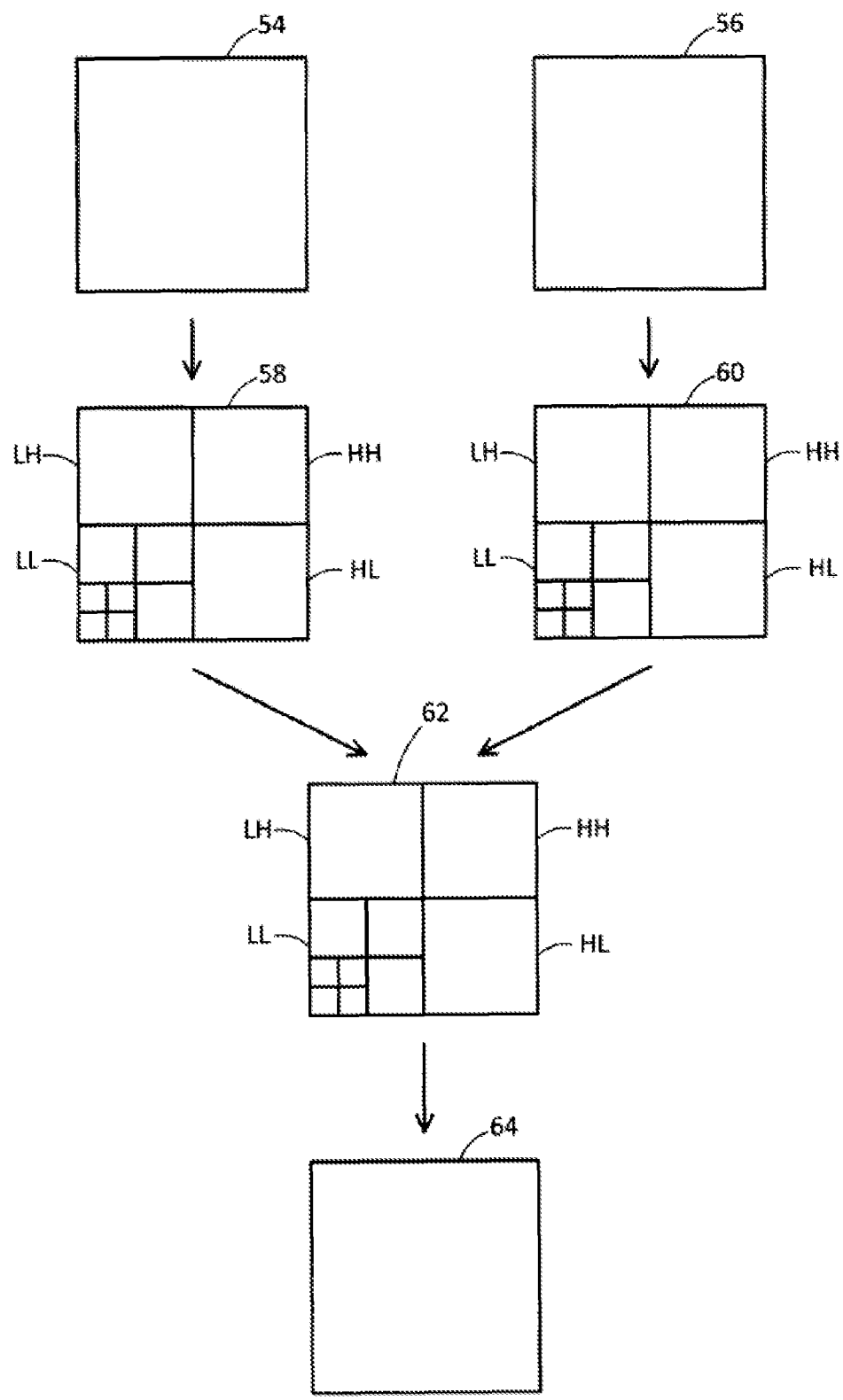

[FIG. 6]
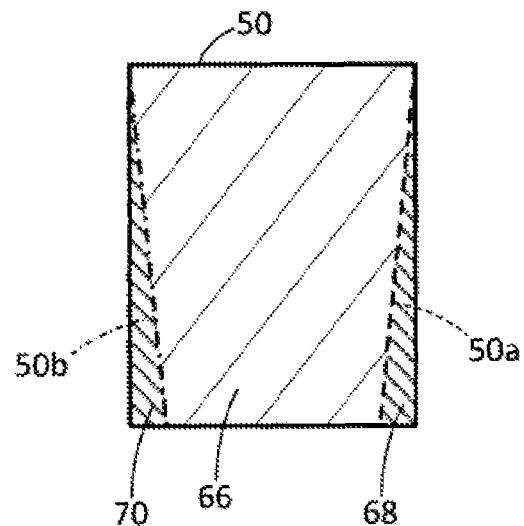
[FIG. 7]
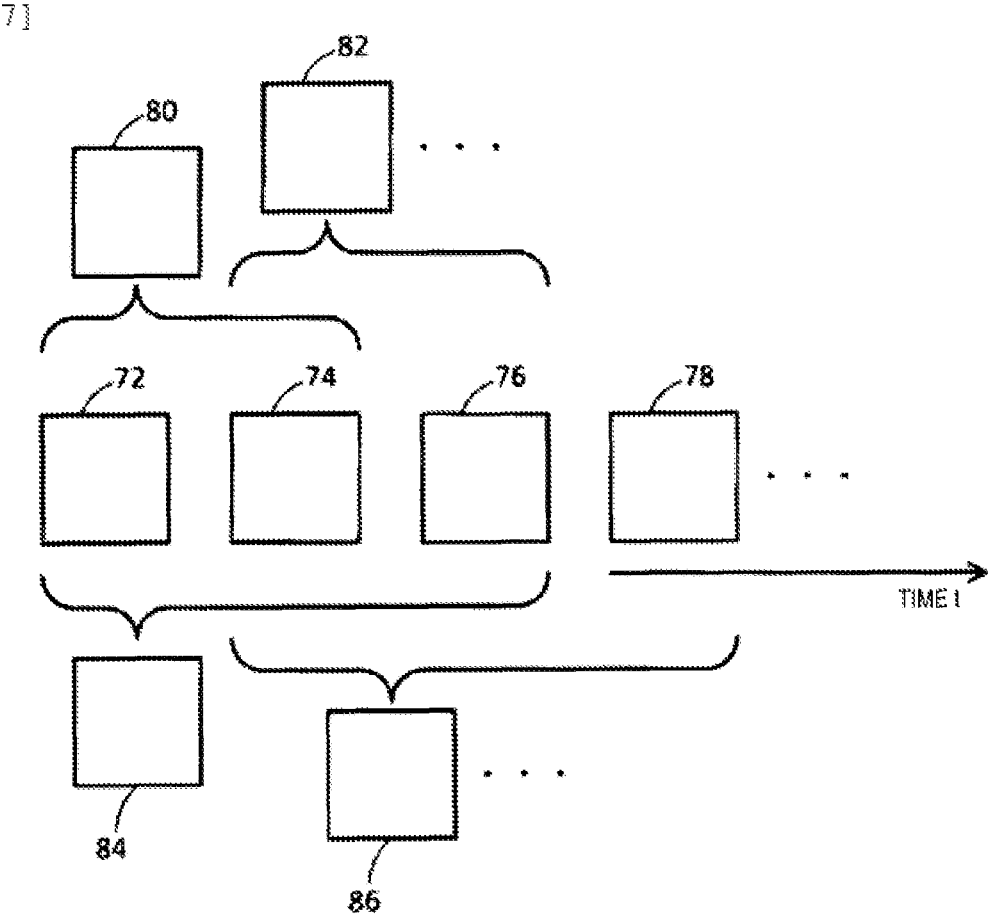

[FIG. 8]
| | | SYNTHESIS METHOD | |
|---|---|---|---|
| | | COMPOUND | PERSISTENCE |
| PROBE TYPE | CONVEX | 0.2 | 0.3 |
| | LINEAR | 0.1 | 0.4 |
| | SECTOR | NA | 0.4 |
[FIG. 9]
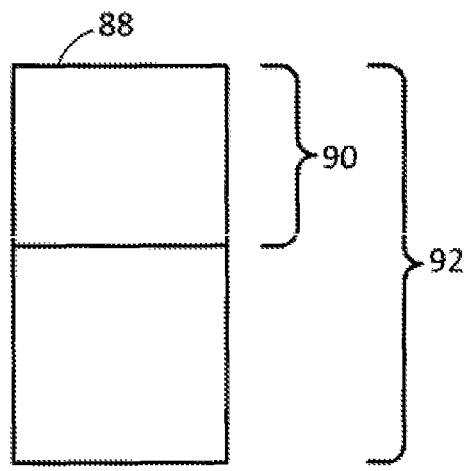

[FIG. 10]
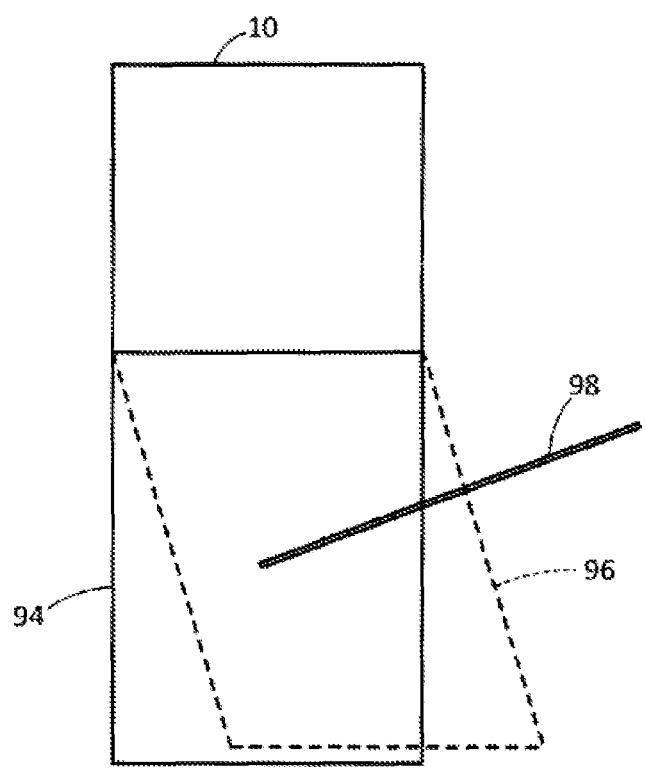

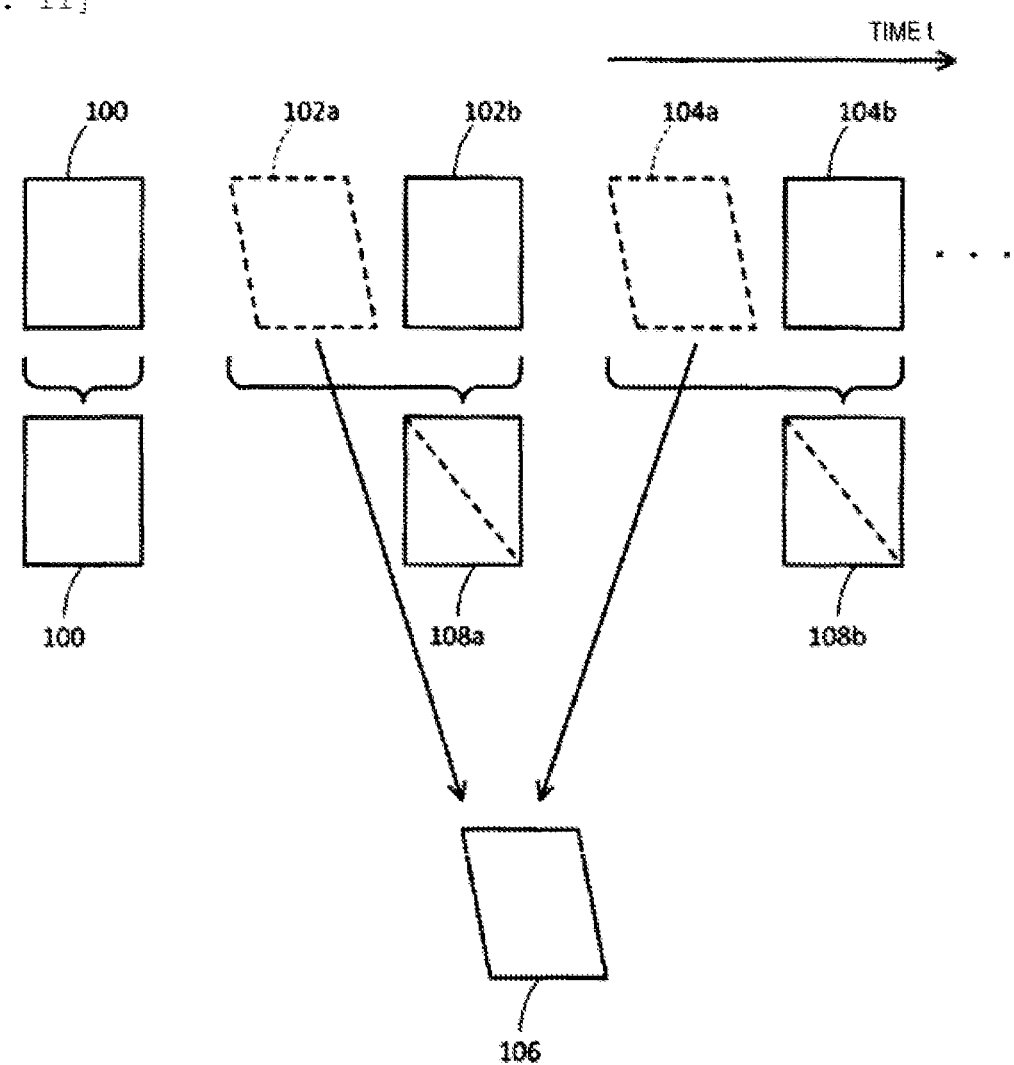

ULTRASONIC DIAGNOSIS DEVICE AND PROGRAM

TECHNICAL FIELD

The present invention relates to an ultrasonic diagnosis device, and particularly to a technique for synthesizing a plurality of images.

BACKGROUND ART

A plurality of frames obtained by transmission/reception of ultrasonic waves may be synthesized in order to equalize an image quality and improve an S/N ratio.

Patent Literatures 1 to 3 disclose image quality improvement methods using a multi-resolution analysis in an ultrasonic diagnosis device.

PRIOR ART LITERATURE

Patent Literature

PTL 1: JP-A-2006-116307
PTL 2: JP-A-2011-56249
PTL 3: JP-A-2015-33569

SUMMARY OF INVENTION

Technical Problem

However, when the plurality of frames are synthesized, since the image is smoothed, an edge portion of an object (for example, a tissue inside a living body) is easily blurred (the image of the edge portion is more likely to be not sharp).

An object of the invention is to generate an output frame where an image of an edge portion is sharpened when the output frame is generated by synthesizing a plurality of frames.

Solution to Problem

The invention is an ultrasonic diagnosis device including a base frame generation unit that generates a base frame by synthesizing a frame sequence obtained by transmission/reception of ultrasonic waves, a compensation frame generation unit that generates a compensation frame where an edge component is emphasized based on the frame sequence, and a synthesis unit that generates an output frame by synthesizing the base frame and the compensation frame.

According to the above configuration, since the compensation frame where the edge component is emphasized and the base frame are synthesized, the output frame where the image of the edge portion is sharpened is generated. The base frame is, for example, a smoothed frame. By synthesizing the compensation frame with such smoothed base frame, it is possible to generate a frame that also synthesizes both the smoothing effect and the sharpening effect. In the synthesis processing according to the synthesis unit, for example, the output frame is generated by performing weighted averaging on the base frame and the compensation frame. In the weighted average, by changing the weighting coefficient for the base frame and the weighting coefficient for the compensation frame, it is possible to generate the output frame according to the purpose. For example, by increasing the weighting coefficient for the base frame, the output frame having a stronger smoothing effect is generated, and by increasing the weighting coefficient for the compensation frame, the output frame having a stronger sharpening effect is generated.

The compensation frame generation unit may generate a component image set which includes a plurality of component images by applying wavelet transform to the frame sequence, and generate the compensation frame by synthesizing and inversely converting the plurality of component images.

The compensation frame generation unit may apply the maximum value method in the synthesis of the plurality of the component images.

The synthesis unit may synthesis the base frame and the compensation frame by changing a weight in an area unit or a pixel unit in the base frame and the compensation frame.

According to the above configuration, the degree of the smoothing effect or the sharpening effect can be adjusted in the area unit or the pixel unit.

Each frame included in the frame sequence may be a frame where the deflection angles of the ultrasonic waves are different from each other, and the synthesis unit may set the weight for an area where the number of frames overlapping each other is small to be smaller than the weight for an area where the number of frames overlapping each other is large in the compensation frame.

The synthesis unit may synthesize the base frame and the compensation frame by changing the weight for each type of an ultrasonic probe in the base frame and the compensation frame.

Each frame included in the frame sequence may be a frame where the deflection angles of the ultrasonic waves are equal to each other and obtained at different times from each other.

The base frame generation unit generates the base frame based on a part of the frame sequence, and the compensation frame generation unit generates the compensation frame based on a larger number of frames than the number of frames used when generating the base frame sequence.

Further, the invention is a program that causes a computer to function as the base frame generation unit that generates the base frame by synthesizing a frame sequence obtained by transmission/reception of ultrasonic waves, a compensation frame generation unit that generates a compensation frame where an edge component is emphasized based on the frame sequence, and a synthesis unit that generates an output frame by synthesizing the base frame and the compensation frame.

Advantageous Effect

According to the invention, when the output frame is generated by synthesizing the plurality of frames, it is possible to generate the output frame where the image of the edge portion is sharpened.

BRIEF DESCRIPTION OF DRAWINGS

FIG. 1 is a block diagram showing an ultrasonic diagnosis device according to a first embodiment of the invention.

FIG. 2 is a block diagram showing a configuration of a synthesis processing unit.

FIG. 3 is a diagram showing an example of scan surfaces according to the first embodiment.

FIG. 4 is a diagram showing an example of reception frames.

FIG. 5 is a diagram showing an example of the reception frame.

FIG. 6 is a diagram showing an example of a compensation frame.

FIG. 7 is a diagram showing an example of reception frames according to a second embodiment.

FIG. 8 is a diagram showing weighting coefficients according to a modification.

FIG. 9 is a diagram showing an example of a reception frame according to a fourth embodiment.

FIG. 10 is a diagram shows an example of a scan surface according to a fifth embodiment.

FIG. 11 is a diagram showing an example of a reception frame according to the fifth embodiment.

DESCRIPTION OF EMBODIMENTS

First Embodiment

FIG. 1 shows an ultrasonic diagnosis device according to a first embodiment of the invention. FIG. 1 is a block diagram showing an overall configuration thereof. The ultrasonic diagnosis device is used in a medical field and has a function of forming an image of tissue inside a living body by transmission/reception of ultrasonic waves.

A probe 10 is an ultrasonic wave transmitter/receiver that transmits and receives the ultrasonic waves. The probe 10 includes, for example, a 1D array transducer. The 1D array transducer is formed by arranging a plurality of vibration elements one-dimensionally. An ultrasound beam is formed by the 1D array transducer and electronically scanned repeatedly. Accordingly, a scan surface is formed in the living body for each electronic scan. The scan surface corresponds to a two-dimensional echo data acquisition space. The probe 10 may include a 2D array transducer formed by two-dimensionally arranging a plurality of vibration elements in place of the 1D array transducer. When the ultrasonic beam is formed by the 2D array transducer and electronically scanned repeatedly, a scan surface as a two-dimensional echo data acquisition space is formed for each electron scan, and when the ultrasonic beam is scanned two-dimensionally, a three-dimensional space is formed as a three-dimensional echo data acquisition space. As a scan method, sector scan, linear scan, convex scan, or the like are used.

The transmission/reception unit 12 functions as a transmission beam former and a reception beam former. At the time of transmission, the transmission/reception unit 12 supplies a plurality of transmission signals having a fixed delay relationship with respect to the plurality of vibration elements included in the probe 10. Accordingly, an ultrasonic transmission beam is formed. At the time of reception, a reflected wave from the inside of the living body is received by the probe 10, and thus a plurality of reception signals are output from the probe to the transmission/reception unit 12. The transmission/reception unit 12 forms a reception beam by applying a phasing addition process to the plurality of reception signals. The beam data is output to the signal processing unit 14. That is, the transmission/reception unit 12 performs delay processing on the reception signal obtained from each vibration element according to a delay processing condition for each vibration element, and performs addition processing of the plurality of reception signals obtained from the plurality of vibration elements to form the reception beam. The delay processing condition is defined by reception delay data (delay time). A reception delay data set (set of delay time) corresponding to the plurality of vibration elements is supplied from the control unit 24. A technology such as transmission aperture synthesis may be used in the transmission/reception of the ultrasonic waves. Further, the transmission/reception unit 12 may execute parallel reception processing.

The ultrasonic beam (transmission beam and reception beam) is electronically scanned by the action of the transmission/reception unit 12, thereby forming the scan surface. The scan surface corresponds to a plurality of beam data, which constitute reception frame data (RF signal frame data). Each of the beam data includes a plurality of echo data arranged in a line in a depth direction. By repeating the electronic scanning of the ultrasonic beam, a plurality of reception frame data arranged in a line on a time axis are output from the transmission/reception unit 12. The plurality of reception frame data form a reception frame sequence.

When the ultrasound beam is two-dimensionally electronically scanned by the action of the transmission/reception unit 12 12, a three-dimensional echo data acquisition space is formed, and volume data as an echo data aggregate is acquired from the three-dimensional echo data acquisition space thereof. By repeating the electronic scanning of the ultrasonic beam, a plurality of volume data arranged in a line on the time axis is output from the transmission/reception unit 12. The plurality of volume data form a volume data sequence.

The signal processing unit 14 is a module that applies signal processing such as wave detection and logarithmic compression with respect to the beam data output from the transmission/reception unit 12. The beam data after the signal processing may be stored in a memory. Of course, the above-described processing may also be applied when the beam data to which such signal processing is not applied is stored in the memory, and the beam data is read.

Further, the signal processing unit 14 includes a synthesis processing unit 16. The synthesis processing unit 16 has functions of generating base frame data by synthesizing the reception frame sequence after the signal processing such as the wave detection and the logarithmic compression, generating compensation frame data where the edge component of the object (for example, the tissue inside the living body) is emphasized based on the reception frame sequence, and generating output frame data by synthesizing the base frame data and the compensation frame data. The output frame data is output to a digital scan converter (DSC) 18. The plurality of output frame data arranged in a line on the time axis are sequentially generated, which constitute an output frame sequence.

The DSC (digital scan converter) 18 includes a convert function (coordinate conversion function, interpolation processing function, and the like). The DSC 18 generates a tissue display frame sequence based on the output frame sequence (reception frame sequence obtained by the synthesis processing unit 16) output from the signal processing unit 14. The individual tissue display frame sequence is data of a B-mode tomographic image. The tissue display frame sequence is displayed on a display unit 22 such as a monitor via a display processing unit 20. Accordingly, the B-mode tomographic image is displayed as a moving image in real time.

The display processing unit 20 performs an overlay processing on graphic data necessary for the tomographic image and the like, thereby generating a display image. The image data is output to the display unit 22, and one or a plurality of images are displayed in a line in a display aspect according to a display mode.

The display unit 22 includes a display device such as a liquid crystal display. The display unit 22 may include a plurality of display devices.

The control unit 24 has a function of performing the operation control of each configuration shown in FIG. 1. The control unit 24 may include a region-of-interest setting unit that sets a region of interest (ROI) on the tissue display frame (B-mode tomographic image).

An input unit 26 is connected to the control unit 24. The input unit 26 includes, for example, an operation panel including an input device such as a trackball, a keyboard, various buttons, various knobs, and the like. A user can specify or input a position of the scan surface, a position of a cross section, an information related to the region of interest, and the like using the input unit 26.

In the above-described ultrasonic diagnosis device, a configuration other than the probe 10 can be realized by using hardware resources such as a processor or an electronic circuit, and a device such as a memory may be used as necessary in the realization. In addition, the configuration other than the probe 10 may be realized by, for example, a computer. In other words, all or part of the configuration other than the probe 10 may be realized by the cooperation of the hardware resources such as a CPU, a memory, a hard disk, and the like, and a software (program) for defining an operation of the CPU and the like included in the computer. The program is stored in a storage device (not shown) via a recording medium such as a CD or a DVD, or via a communication path such as a network. As another example, the configuration other than the probe 10 may be realized by a Digital Signal Processor (DSP), a Field Programmable Gate Array (FPGA), or the like. Of course, a Graphics Processing Unit (GPU) or the like may also be used.

Hereinafter, the ultrasonic diagnosis device according to the first embodiment will be described in detail. As an example, it is assumed that the probe 10 includes the 1D array transducer.

The synthesis processing unit 16 will be described in detail below with reference to FIG. 2. FIG. 2 is the block diagram showing a configuration of the synthesis processing unit 16.

The synthesis processing unit 16 includes a memory 28, a basic image generation unit 30 as an example of a base frame generation unit, an edge-enhanced image generation unit 32 as an example of a compensation frame generation unit, and a synthesis unit 34.

The memory 28 includes a ring buffer which includes, for example, a buffer F1, F2, . . . , Fn, and stores the plurality of reception frame data after the signal processing such as detection and logarithmic compression is applied. The ring buffer includes, for example, buffers corresponding to the number of reception frames to which the processing by the basic image generation unit 30 and the edge-enhanced image generation unit 32 is applied. Of course, the ring buffer may include a larger number of buffers than the number of the buffers.

The basic image generation unit 30 acquires the plurality of reception frame data of a processed object from the memory 28, and generates the base frame data by synthesizing the plurality of reception frame data. The basic image generation unit 30 generates the base frame data by simply averaging the plurality of reception frame data, for example. That is, the basic image generation unit 30 generates the base frame data by adding the plurality of reception frame data (e.g. luminance value) for each pixel and dividing the sum by the number of the plurality of reception frames. The basic image generation unit 30 generates the base frame data representing a smoothed image by applying such smoothing processing to the reception frame data. The number of reception frames as the processed object is determined in advance. Of course, the number of reception frames as the processed object may be changed to an arbitrary value by the user, may be changed according to the mode of ultrasonic diagnosis, or may be changed according to the type of the probe 10. The processing by the basic image generation unit 30 will be described in detail later.

The edge-enhanced image generation unit 32 acquires a plurality of reception frame data of the processed object from the memory 28, and generates the compensation frame data where the edge component of the object is emphasized based on the plurality of reception frame data. The edge-enhanced image generation unit 32 generates the compensation frame data by performing a Wavelet Fusion method on the plurality of reception frame data, for example. That is, the edge-enhanced image generation unit 32 generates a component image set which includes a plurality of component-specific images by applying a wavelet transform to the plurality of reception frame data, and generates the compensation frame data by synthesizing and inversely converting the plurality of component-specific image data. In the synthesis, for example, the maximum value method is applied. The processing by the edge-enhanced image generation unit 32 will be described in detail later.

The number of reception frames processed by the edge-enhanced image generation unit 32 may be equal to, or more than, or less than the number of reception frames processed by the basic image generation unit 30. For example, the relationship between the number of the reception frames processed by the edge-enhanced image generation unit 32 and the number of reception frames processed by the basic image generation unit 30 may be changed according to the mode of the ultrasound diagnosis.

The synthesis unit 34 generates the output frame data by synthesizing the base frame data and the compensation frame data. Specifically, the synthesis unit 34 generates the output frame data by performing weighted averaging on the base frame data and the compensation frame data. That is, for each pixel, the synthesis unit 34 multiplies the base frame data (for example, the luminance value) by a weighting coefficient for the base frame, multiplies the compensation frame data (for example, the luminance value) by a weighting coefficient for the compensation frame, adds results of these multiplications, and divides a value obtained from the addition by the sum of the weighting coefficients. Accordingly, a weighted average value (for example, the luminance value) of each pixel is calculated, and the output frame data is generated. The weighting coefficient may be determined by the user, may be determined for each area in the frame, may be determined for each pixel in the frame, or may be determined according to the type of the probe 10. As an example, the weighting coefficient for the base frame is "0.7", and the weighting coefficient for the compensation frame is "0.3". Of course, these values are merely one example, and other values may also be used. The processing by the synthesis unit 34 will be described in detail later.

The output frame data generated by the synthesis unit 34 is output to the DSC 18. When the reception frame data is sequentially generated by transmission/reception of the ultrasonic waves, the base frame data is sequentially generated by the basic image generation unit 30, the compensation frame data is sequentially generated by the edge-enhanced image generation unit 32, and the output frame data is sequentially generated by the synthesis unit 34. Accordingly, the output frame sequence which includes a plurality of output frame data arranged in a line on the time axis is configured.

A spatial compound method is applied in the first embodiment. Hereinafter, the spatial compound method will be described in detail. FIG. 3 shows an example of the scan surfaces in a case where the spatial compound method is applied. When the spatial compound method is applied, the plurality of scan surfaces having different deflection angles of the ultrasonic beams are formed. In the example shown in FIG. 3, three scan surfaces (scan surfaces 36, 38, 40) are formed. The scan surfaces 36, 38, 40 are two-dimensional planes formed by transmission/reception of the ultrasonic beam.

An example of the scan surface 36 is a scan surface formed at a position where a deflection angle θ is zero degree (0 degree). For example, a switch for giving an instruction to form the scan surface 36 with the deflection angle θ being zero degree is provided in the input unit 26, and when the switch is pressed by the user, the scan surface 36 is formed at the position where the deflection angle θ is zero degree. The tissue display frame (B-mode tomographic image) on the scan surface 36 is generated and displayed on the display unit 22. The user can change an orientation and a position of the probe 10 such that a site of an observed object appears in the B-mode tomographic image while observing the B-mode tomographic image. Of course, when the probe 10 including the 2D array transducer is used, the scan surface may also be set to electronically deflecting the scan surface. For example, a knob or a trackball for deflecting the scan surface is provided on the input unit 26, and when the knob or the trackball is operated by the user, the scan surface is deflected.

The scan surface 38 is a scan surface that is electronically deflected in a +θ direction with reference to the position of the scan surface 36. The scan surface 40 is a scan surface that is electronically deflected in a −θ direction with reference to the position of the scan surface 36. For example, the knob or the trackball for deflecting the scan surface is operated by the user, and the scan surfaces 38, 40 are set at positions corresponding to the operation. The tissue display frame (B-mode tomographic image) on the scan surface 38, 40 may be generated and displayed on the display unit 22.

An example of the scan surface 38 is a scan surface where the deflection angle is formed at a position of +5 degrees, and the scan surface 40 is a scan surface where the deflection angle is formed at a position of −5 degrees.

For example, the ultrasonic beam is repeatedly transmitted and received while changing the deflection angle such that the scan surfaces are repeatedly formed in an order of the scan surfaces 36, 38, 40. Accordingly, the scan surfaces are repeatedly formed in the order of the scan surface 36, 38, 40. The scan surface 36 is a scan surface formed at a time t0, the scan surface 38 is a scan surface formed at a time t1, and the scan surface 40 is a scan surface formed at a time t2.

In the example shown in FIG. 3, three scan surfaces are set, but a plurality of scan surfaces other than 3 (for example, two or more scan surfaces) may also be formed.

FIG. 4 shows a reception frame acquired from each scan surface. The reception frame is data input to the synthesis processing unit 16 after being subjected to the signal processing such as the wave detection and the logarithmic compression by the signal processing unit 14.

When the ultrasonic beam is transmitted and received with the scan surface 36 as the object, a reception frame 42 (frame indicated by a solid line) is generated. When the ultrasonic beam is transmitted and received with the scan surface 38 as the object, a reception frame 44 (frame indicated by a broken line) is generated. When the ultrasonic beam is transmitted and received with the scan surface 40 as the object, a reception frame 46 (frame indicated by a one-dot chain line) is generated. The reception frames 42, 44, 46 are stored in the memory 28. When the ultrasonic beam is repeatedly transmitted and received with the scan surfaces 36, 38, 40 as the objects, the reception frames 42, 44, 46 are sequentially generated. The reception frames 42, 44, 46 form the reception frame sequence arranged in a line on the time axis.

The basic image generation unit 30 generates a base frame 48 by simply averaging the reception frame 42 obtained from the scan surface 36, the reception frame 44 obtained from the scan surface 38, and the reception frame 46 obtained from the scan surface 40. The base frame 48 corresponds to a compound image. In the compound image, the image is smoothed. In the example shown in FIG. 4, the base frame 48 has a display region the same as a display region of the reception frame 42 obtained from the scan surface 36 with the deflection angle being 0 degree. That is, the base frame 48 is a frame corresponding to the scan surface 36, and a shape, a size, and a position of the base frame 48 are the same as the shape, the size, and the position of the reception frame 42.

Since the scan surfaces 36, 38, 40 are scan surfaces where the deflection angles of the ultrasonic beams are different from each other, the base frame 48 includes a region where three reception frames (reception frames 42, 44, 46) are added, and a region where two reception frames (reception frames 42, 44, or reception frames 42, 46) are added. In this case, a striped pattern (for example, an elongated linear pattern) may appear on boundaries 48a, 48b between the region where the three reception frames are added and the region where the two reception frames are added. The boundary 48a corresponds to the boundary between the addition region of the three reception frames and the addition region of the two reception frames (reception frames 42, 46), and the boundary 48b corresponds to the boundary between the addition region of the three reception frames and the addition region of the two reception frames (reception frames 42 and 44). For example, the appearance of the pattern can be suppressed or prevented by performing weighting processing on the boundaries 48a, 48b, and the periphery thereof.

The edge-enhanced image generation unit 32 generates a compensation frame 50 by applying the wavelet fusion method to the reception frame 42 obtained from the scan surface 36, the reception frame 44 obtained from the scan surface 38, and the reception frame 46 obtained from the scan surface 40. The compensation frame 50 corresponds to a wavelet fusion image. Since the wavelet transform is applied, the image is sharpened in the compensation frame 50, and the edge component of the object is clearly represented. In the example shown in FIG. 4, the compensation frame 50 has a display region the same as the display region of the reception frame 42 obtained from the scan surface 36 with the deflection angle being 0 degree. That is, the compensation frame 50 is a frame corresponding to the scan surface 36, and the shape, size, and position of the compensation frame 50 are the same as the shape, size, and position of the reception frame 42.

Similarly to the base frame 48, in the compensation frame 50, the striped pattern may appear in the boundaries 50a, 50b between the synthesized region of the three reception frames (the reception frames 42, 44, 46) and the synthesized region of the two reception frames. The boundary 50a corresponds to the boundary between the synthesized region of the three reception frames and the synthesized region of the two reception frames (reception frames 42, 46), and the boundary 50b corresponds to the boundary between the synthesized region of the three reception frames and the synthesized region of the two reception frames (reception frame 42, 44). Since the compensation frame 50 (wavelet fusion image) is a sharpened image, the edge component of the object is emphasized by the boundaries 50a, 50b, and a striped pattern is likely to appear. In order to cope with this, the appearance of the pattern can be suppressed or prevented by performing weighting processing on the boundaries 50a, 50b, and the periphery thereof.

The synthesis unit 34 generates the output frame 52 by performing weighted averaging on the base frame 48 and the compensation frame 50. For example, for each pixel, the synthesis unit 34 multiplies the data (e.g., luminance value) of the base frame 48 by the weighting coefficient for the base frame (e.g., 0.7) and multiplies the data (e.g., luminance value) of the compensation frame 50 by the weighting coefficient for the compensation frame (e.g., 0.3), adds the results of the multiplication, and divides the value obtained by the addition by the sum of the weighting coefficients (e.g., 1.0). Accordingly, the weighted average value (for example, the luminance value) of each pixel is calculated, and the output frame 52 is generated. The above weighting coefficient is an example, and other values may also be used.

Conversion processing is applied to the output frame 52 by the DSC 18, and thus the tissue display frame (B-mode tomographic image) is generated. A plurality of output frames 52 arranged in a line on the time axis are sequentially generated, and a plurality of tissue display frames arranged on the time axis are sequentially generated. The tissue display frame is displayed on the display unit 22 via the display processing unit 20.

The output frame 52 is a frame generated by synthesizing the smoothed base frame 48 and the sharpened compensation frame 50. Therefore, in the output frame 52, a smoothed tissue image is represented and the edge component of the tissue is sharpened.

The wavelet fusion method executed by the edge-enhanced image generation unit 32 will be described below with reference to FIG. 5. FIG. 5 shows a frame at each stage. As an example, a case where the wavelet fusion method is applied to the reception frames 54, 56 will be described.

First, the edge-enhanced image generation unit 32 applies the wavelet transform (for example, Dual Tree Complex Wavelet Transform (DT-CWT): parallel tree complex wavelet transform) to the reception frame 54 to generate a component image set 58 including the plurality of component-specific images. Specifically, the edge-enhanced image generation unit 32 applies a low-pass filter and a high-pass filter to the reception frame 54 in a vertical direction and a horizontal direction, and executes this application to the third order to generate the component image set 58. The component image set 58 is a set of an HH component image, an HL component image, an LH component image, and an LL component image. The wavelet transform is further applied to the LL component image.

Similarly, the edge-enhanced image generation unit 32 applies the wavelet transform to the reception frame 56 to generate a component image set 60 which includes the plurality of component images. The component image set 60 is also a set obtained by executing the wavelet transform to the third order, and is a set of the HH component image, the HL component image, the LH component image, and the LL component image. The wavelet transform is further applied to the LL component image.

In the above example, although the wavelet transform is executed to the third order, this is merely an example, and the wavelet transform may be executed to a higher-order order. For example, the order may be changed according to the type of the probe 10.

Next, the edge-enhanced image generation unit 32 generates a synthesized component image set 62 by synthesizing the component image set 58 and the component image set 60. In the synthesis, for example, the maximum value method is applied. That is, the edge-enhanced image generation unit 32 selects a maximum value (for example, a maximum value of the luminance value (the value corresponding to the coefficient) from the component image set 58 and the component image set 60 for each pixel, and generates the synthesized component image set 62 constituted by the maximum value of each pixel. The synthesized component image set 62 is also the set of the HH component image, the HL component image, the LH component image, and the LL component image.

Next, the edge-enhanced image generation unit 32 inverse transforms (DT-CWT$^{-1}$) the synthesized component image set 62. Accordingly, an edge-enhanced image 64 where an edge component in the tissue is emphasized is generated. The edge-enhanced image 64 corresponds to the compensation frame.

In the example shown in FIG. 4, the wavelet fusion method shown in FIG. 5 is applied to the reception frames 42, 44, 46, and the compensation frame 50 as the edge-enhanced image is generated.

As described above, according to the first embodiment, by synthesizing the smoothed base frame 48 and the compensation frame 50 where the edge component is sharpened, the output frame 52 where the edge component of the object is sharpened and an image of the smoothed object (for example, the tissue inside the living body) is represented is generated.

In general, when an ultrasonic beam is transmitted and received in parallel to the edge portion of the object, the edge portion of an image obtained by the transmission/reception wave is hard to be emphasized. Since the image is smoothed in the compound image obtained by simply averaging the plurality of reception frames, the S/N and the connection of the images become good, but the image of the edge portion is more easily blurred. Therefore, in the base frame 48, the image of the edge portion is easily blurred (the image of the edge portion is more likely to be not sharp).

In the first embodiment, the compensation frame 50 where the image of the edge portion is sharpened is generated in addition to the base frame 48, and the compensation frame 50 and the base frame 48 are synthesized. Accordingly, the frame where the edge component of the object is sharpened is obtained while the image of the smoothed object is represented.

In the first embodiment, the synthesis processing by the synthesis processing unit 16 is applied to the frame data before the conversion processing by the DSC 18 is applied, but the synthesis processing may be applied to the tissue display frame data (B-mode tomographic image data) after the conversion processing is applied without applying the synthesis processing to the frame data before the conversion processing is applied.

Further, in the example shown in FIG. 4, the base frame and the compensation frame are generated based on the three reception frames, but the base frame and the compensation frame may be generated based on reception frames having a number other than three (for example, two or more reception frames). The number of reception frames for generating the compensation frame may be equal to, more than, or less than the number of the reception frames for generating the base frame.

The weighting coefficient applied when synthesizing the base frame and the compensation frame may be set in an area unit. That is, the weighting coefficient may be set for each area. For example, a different weighting coefficient may be used in each area.

The weighting coefficient set for each area will be described in detail below with reference to FIG. 6. FIG. 6 shows an example of the compensation frame. As described with reference to FIG. 4, since the compensation frame 50 as the wavelet fusion image is the sharpened image, the edge component of the object is emphasized at the boundaries 50a, 50b of each reception frame, and the striped pattern is likely to appear. In order to cope with this, in the compensation frame 50, a first weighting coefficient applied to the area where a larger number of reception frames are synthesized objects and a second weighting coefficient applied to the area where a smaller number of reception frames are synthesized object may be made different. For example, a value smaller than the first weighting coefficient is used as the second weighting coefficient.

In the example shown in FIG. 6, an area 66 in the compensation frame 50 is the area where the three reception frames (reception frames 42, 44, 46) are synthesized objects, and an area 68 is the area where the two reception frames (reception frames 42, 46) are synthesized objects, and the area 70 is the area where the two reception frames (reception frames 42, 44) are synthesized objects. In this case, the synthesis unit 34 applies the second weighting coefficient having the value smaller than the first weighting coefficient applied to the area 66 to the areas 68, 70 to generate an output frame 52 by performing weighted averaging on the base frame 48 and the compensation frame 50.

For example, "0.3" is applied to the area 66 in the compensation frame 50 as the first weighting coefficient, and "0.1" is applied to the areas 68, 70 in the compensation frame 50 as the second weighting coefficient. Accordingly, "0.7" is applied to the area corresponding to the area 66 in the base frame 48 as the weighting coefficient, and the weighting coefficient "0.9" is applied to the area corresponding to the areas 68, 70 in the base frame 48. The synthesis unit 34 applies such weighting coefficients to the base frame 48 and the compensation frame 50 to perform the weighted averaging. Accordingly, the output frame 52 having the weighting coefficient different in each area is generated.

As described above, by using a value smaller than the first weighting coefficient applied to the area 66 as the second weighting coefficient applied to the areas 68, 70, since the contribution of the data in the areas 68, 70 becomes smaller, the edge component of the object is difficult to be emphasized at the boundaries 50a, 50b, and the occurrence of the striped pattern can be suppressed or prevented.

As another example, the weighting coefficient applied when synthesizing the base frame and the compensation frame may be set in a pixel unit. That is, the weighting coefficient may be set for each pixel. For example, a different weighting coefficient may be used for each pixel. In the example shown in FIG. 6, for example, a value smaller than the weighting coefficient applied to the pixel included in the area 66 may be used as the weighting coefficient applied to the pixel included in the areas 68, 70. As another example, a value smaller than the weighting coefficient applied to a pixel other than the pixel group may be used as the weighting coefficient applied to a pixel group on the boundaries 50a, 50b, or a value smaller than the weighting coefficient applied to the pixel other than the pixel group may be used as the weighting coefficient applied to the pixel group on and around the boundaries 50a, 50b (for example, a range of a predetermined number of pixels from the boundaries 50a, 50b). In this way, by changing the weighting coefficient, the edge component of the object is difficult to be emphasized by the boundaries 50a, 50b, and the occurrence of the striped pattern can be suppressed or prevented.

As still another example, the weighting coefficients applied to the base frame and the compensation frame may be changed according to variation in the luminance values of the plurality of reception frames (for example, the reception frames 42, 44, 46) to be the object of the synthesis processing. The variation may be evaluated, for example, by variance of the luminance values, a difference between a maximum value and a minimum value of the luminance values of the plurality of frames, and the like. For example, if the variance of the luminance values is less than or equal to a predetermined threshold, it is determined that there is no variation or the variation is small, and if the variance is larger than the threshold, it is determined that the variation is large. Similarly, when the difference between the maximum value and the minimum value is less than or equal to the predetermined threshold, it is determined that there is no variation or the variation is small, and if the difference is larger than the threshold, it is determined that the variation is large. This determination is performed by the synthesis unit 34, for example.

When there is no variation in the luminance value or the variation in the luminance value is small, the synthesis unit 34 uses a larger value as the weighting coefficient applied to the base frame, and uses a smaller value as the weighting coefficient applied to the compensation frame. When the variation in the luminance value is large, the synthesis unit 34 uses the smaller value as the weighting coefficient applied to the base frame, and uses the larger value as the weighting coefficient applied to the compensation frame. At this time, the synthesis unit 34 may set the weighting coefficient for each pixel. When the variation in the luminance value is large, it is possible to suppress the variation in the output frame by reducing the weighting coefficient applied to the base frame.

In addition, the synthesis unit 34 may generate the output frame using data in the area 66 without using the data in the areas 68, 70 in the compensation frame 50. In this case, the synthesis unit 34 may generate output data using the data in the area corresponding to the area 66 without using the data in the area corresponding to the areas 68, 70 in the base frame 48, or may generate the output data by using the data in the area corresponding to the areas 68, 70 in addition to the area 66.

When the weighting coefficients are changed for each area or for each pixel, a weighting coefficient set indicating a set of weighting coefficients for each area or each pixel may be created in advance, and a plurality of weighting coefficient sets each with different weighting coefficients may be created in advance. In this case, the user may select a target weighting coefficient set from the plurality of weighting coefficient sets, or the synthesis unit 34 may select the target weighting coefficient set.

In the case where the probe 10 is moved, the synthesis unit 34 may stop the synthesis processing of the base frame and the compensation frame, further reduce the weighting coefficient of the compensation frame, and further increase the weighting coefficient of the base frame. Accordingly, it is possible to suppress or prevent an unnatural edge afterimage caused by a movement of the probe 10. For example, the motion of the probe 10 can be detected by calculating an inter-frame difference value or an inter-frame correlation value for the reception frame or the tissue display frame. When the difference value or the correlation value is equal to or larger than the predetermined threshold, it is determined that the probe 10 is moved, and the weighting coefficient of the compensation frame is made small.

Second Embodiment

An ultrasonic diagnosis device according to a second embodiment of the invention will be described below. The ultrasonic diagnosis device according to the second embodiment has the same configuration as the ultrasonic diagnosis device according to the first embodiment. The spatial compound method is applied in the first embodiment, but a persistence method rather than the spatial compound method is applied in the second embodiment.

Hereinafter, the persistence method will be described in detail with reference to FIG. 7. FIG. 7 shows an example of the reception frames. In the persistence method, synthesis processing by the synthesis processing unit 16 is applied to the plurality of reception frames arranged in a line on the time axis. The deflection angle of the ultrasonic beam is set to the predetermined angle (for example, 0 degree), and the scan surface having the deflection angle is formed to generate the reception frame sequence. Hereinafter, an example of the deflection angle is assumed to be 0 degree.

In the example shown in FIG. 7, the reception frames 72, 74, 76, 78 and the like are sequentially generated, and constitute the reception frame sequence arranged in a line on the time axis. These are reception frames obtained from the same scan surface. In addition, each reception frame is the data after the signal processing such as the wave detection, the logarithmic compression and the like which is applied by the signal processing unit 14, and is the data input to the synthesis processing unit 16.

In the second embodiment, the basic image generation unit 30 generates the base frame by simply averaging the predetermined number of the reception frames (for example, two reception frames). The basic image generation unit 30 generates a plurality of base frames arranged in a line on the time axis by performing simply averaging while changing the plurality of reception frames which are the object of the simple average processing along a time direction (frame direction). That is, the basic image generation unit 30 generates the plurality of base frames by obtaining the moving average in the time direction. The number of reception frames as the object of the simply averaging may be changed to the arbitrary value by the user.

In the example shown in FIG. 7, the basic image generation unit 30 generates the base frame 80 by simply averaging the reception frames 72, 74. Next, the basic image generation unit 30 generates the base frame 82 by simply averaging the next two reception frames (the reception frames 74, 76) on the time axis. The basic image generation unit 30 sequentially generates a plurality of base frames arranged in a line on the time axis by repeating this processing.

In addition, the edge-enhanced image generation unit 32 generates a compensation frame by applying the wavelet fusion method to the predetermined number of reception frames (for example, three reception frames). The edge-enhanced image generation unit 32 generates the plurality of compensation frames arranged in a line on the time axis by performing the wavelet fusion method while changing the plurality of reception frames to which the wavelet fusion method is applied along the time direction. The number of reception frames to which the wavelet fusion method is applied may be changed to the arbitrary value by the user.

In the example shown in FIG. 7, the edge-enhanced image generation unit 32 generates the compensation frame 84 by applying the wavelet fusion method to the reception frames 72, 74, 76. Next, the edge-enhanced image generation unit 32 generates the compensation frame 86 by applying the wavelet fusion method to the next three reception frames (the reception frames 74, 76, 78) on the time axis. The edge-enhanced image generation unit 32 sequentially generates the plurality of compensation frames arranged on the time axis by repeating this processing.

The synthesis unit 34 sequentially performs weighted averaging on a plurality of base frames and compensation frames arranged on the time axis to sequentially generate the plurality of output frames. In the example shown in FIG. 7, the synthesis unit 34 generates the output frame by performing weighted averaging on the base frame 80 and the compensation frame 84, and generates the output frame by performing weighted averaging on the base frame 82 and the compensation frame 86. The synthesis unit 34 repeats this processing to generate the plurality of output frames arranged in a line on the time axis.

In the persistence method, the number of reception frames for generating the base frames may be smaller than the number of reception frames for generating the compensation frames. In the example shown in FIG. 7, the base frames are generated based on the two reception frames, and the compensation frames are generated based on the three reception frames. The base frames are more likely to be affected by the motion of the object than the compensation frames since being generated by the simply averaging. In order to cope with this, by reducing the number of reception frames for generating the base frames, responsiveness to the movement of the object is improved, and therefore, even when the simply averaging is performed, the blur of the image can be prevented.

In addition, a processing according to an Infinite Impulse Response (IIR) method may be performed in the persistence method. In this case, since the weight of the latest reception frame is the largest, the responsiveness is improved.

(Modification)

A modification of the first and the second embodiments will be described below with reference to FIG. 8. FIG. 8 shows an example of the weighting coefficients applied to the base frame and the compensation frame when the synthesis processing (weighted average processing) is performed by the synthesis unit 34.

In the modification, the synthesis unit 34 changes the weighting coefficient applied at the time of the weighted average processing in accordance with the type of the probe 10 used.

First, the weighting coefficients in a case where the compound method as the synthesis method according to the first embodiment is applied will be described. When a convex type probe is used as the probe 10, "0.2" is used as the weighting coefficient applied to the compensation frame, and "0.8" is used as the weighting coefficient applied to the base frame. In this case, the synthesis unit 34 multiplies the compensation frame data (e.g., the luminance value) by the weighting coefficient "0.2", multiplies the base frame data (e.g., the luminance value) by the weighting coefficient "0.8" for each pixel, adds the results of the multiplication, and divides the value obtained by the addition by the sum (1.0) of the weighting coefficients. As a result, a weighted average value (for example, the luminance value) of each pixel is calculated, and the output frame data is generated. When a linear type probe is used as the probe 10, "0.1" is used as the weighting coefficient applied to the compensation frame, and "0.9" is used as the weighting coefficient applied to the base frame.

Next, the weighting coefficients in a case where the persistence method as the synthesis method according to the second embodiment is applied will be described. When a convex type probe is used as the probe 10, "0.3" is used as the weighting coefficient applied to the compensation frame, and "0.7" is used as the weighting coefficient applied to the base frame. When a linear type probe is used as the probe 10, "0.4" is used as the weighting coefficient applied to the compensation frame, and "0.6" is used as the weighting coefficient applied to the base frame. When a sector type probe is used as the probe 10, "0.4" is used as the weighting coefficient applied to the compensation frame, and "0.6" is used as the weighting coefficient applied to the base frame.

As described above, according to the type of the probe 10 used, an appropriate image suitable for the type of the probe 10 is generated by changing the weighting coefficients used in the weighted average processing by the synthesis unit 34. For example, since the frame rate and the probe shape are different depending on the type of the probe 10, an appropriate image is generated by changing the weighting coefficient according to the frame rate and the probe shape.

For example, the range where the deflection angle of the ultrasonic beam can be changed differs depending on the type of the probe 10, and the weighting coefficients may be determined according to the variable range. For example, when the probe 10 with a narrow variable range is used, a larger value may be used as the weighting coefficient applied to the compensation frame, as compared with the case where the probe 10 having a wide variable range is used.

The values of the weighting coefficients shown in FIG. 8 are merely examples, and the weighting coefficients may be changed according to the individual characteristics of the probe 10.

The data indicated by a weighting coefficient table shown in FIG. 8 may be stored in a storage unit (not shown). In this case, the synthesis unit 34 may automatically detect the type of the probe 10 connected to an ultrasonic diagnosis device main body, and acquire the weighting coefficients corresponding to the type from the weighting coefficient table. For example, when the probe 10 is connected to the ultrasonic diagnostic apparatus main body, the synthesis unit 34 acquires the information indicating the probe type stored in the memory in the probe 10 from the memory, and acquires the weighting coefficient corresponding to the probe type indicated by the information from the weighting coefficient table. Of course, the user may use the input unit 26 to input information indicating the type of the probe 10. In this case, the synthesis unit 34 acquires the weighting coefficients corresponding to the type of the probe 10 indicated by the information input by the user from the weighting coefficient table.

Third Embodiment

An ultrasonic diagnosis device according to a third embodiment of the invention will be described below. The ultrasonic diagnostic apparatus according to the third embodiment has the same configuration as the ultrasonic diagnosis device according to the first embodiment. In the third embodiment, the synthesis processing unit 16 performs processing on a plurality of reception frames obtained at different sound velocities.

In the third embodiment, the transmission/reception unit 12 performs the delay processing in accordance with a plurality of different delay processing conditions (reception delay data set) to form a plurality of reception frame data obtained each at a different sound velocity.

Three types of sound velocities are used as one example. The first sound velocity is 1460 m/s, the second sound velocity is 1360 m/s, and the third sound velocity is 1560 m/s. Of course, a plurality of types of sound velocities other than the three types may be used. In addition, the values of the sound velocities are merely an example, and the values of the sound velocities may be changed according to an imaging object or the like. The transmission/reception unit 12 12 repeatedly performs transmission/reception processing while changing the sound speed in an order of the first sound velocity, the second sound velocity, and the third sound velocity. Accordingly, a plurality of reception frames arranged in a line on the time axis are formed.

The edge-enhanced image generation unit 32 generates the compensation frame data by applying the wavelet fusion method to the reception frame data obtained at the first sound velocity, the reception frame data obtained at the second sound velocity, and the reception frame data obtained at the third sound velocity, as in the first embodiment. The edge-enhanced image generation unit 32 generates the compensation frame data each time the reception frame data at each sound velocity is formed. Accordingly, the plurality of compensation frames arranged on the time axis are formed.

In the third embodiment, the basic image generation unit 30 does not perform the processing.

The synthesis unit 34 generates the output frame data by performing weighted averaging of the reception frame data obtained at a specific sound velocity (for example, the reception frame data obtained at the first sound velocity) and the compensation frame data.

According to the third embodiment, even when the reception frame is generated by changing the sound velocity, the image where the edge portion of the object is sharpened is obtained by using the compensation frame.

Fourth Embodiment

An ultrasonic diagnosis device according to a fourth embodiment of the invention will be described below. The ultrasonic diagnosis device according to the fourth embodiment has the same configuration as the ultrasonic diagnosis device according to the first embodiment. Multistage focus processing is executed in the fourth embodiment.

A plurality of reception frame data having different focus is generated according to the focus control of the ultrasonic beam by the transmission/reception unit 12. For example, the first focus and the second focus are set, and the transmission/reception unit 12 repeatedly performs the transmission/reception processing while alternately changing the focus of the ultrasonic beam between the first focus and the second focus. Accordingly, a plurality of reception frames arranged in a line on the time axis are formed.

In FIG. 9, a reception frame obtained in each focus is shown. For example, the reception frame 90 is the reception frame obtained in the first focus, and the reception frame 92 is the reception frame obtained in the second focus.

The edge-enhanced image generation unit 32 generates the compensation frame data by applying the wavelet fusion method to the reception frame 90 obtained in the first focus and the reception frame 92 obtained in the second focus as the object as in the first embodiment. The edge-enhanced image generation unit 32 generates the compensation frame data each time the reception frame data is generated. Accordingly, the plurality of compensation frames arranged on the time axis are formed.

In the fourth embodiment, the basic image generation unit 30 does not perform the processing.

The synthesis unit 34 generates the output frame data by performing weighted averaging on the reception frame data obtained in a specific focus (for example, the reception frame 90 obtained in the first focus) and the compensation frame data.

According to the fourth embodiment, even when the multistage focus processing is executed, the image where the edge portion of the object is sharpened can be obtained by using the compensation frame. In the above example, the focus is changed to two stages, however, the focus may also be changed to three or more stages.

In addition, also in the fourth embodiment, the synthesis unit 34 may perform weighted averaging by changing the weighting coefficient in the area unit or in the pixel unit of.

Fifth Embodiment

An ultrasonic diagnosis device according to a fifth embodiment of the invention will be described below. The ultrasonic diagnosis device according to the fifth embodiment has the same configuration as the ultrasonic diagnosis device according to the first embodiment. In the fifth embodiment, the synthesis processing unit 16 performs the processing on a plurality of reception frames obtained by transmission/reception of the ultrasonic waves having different frequencies from each other.

The transmission/reception unit 12 generates the reception frame data (reception frame data which includes a THI (Tissue Harmonic Imaging) component) which includes a harmonic component by transmission/reception of the ultrasonic waves having a relatively high frequency, for example, and generates the reception frame data which includes a fundamental wave component by transmission/reception of the ultrasonic waves having a relatively low frequency.

The transmission/reception unit 12 alternately repeats transmission/reception of the ultrasonic waves having a relatively high frequency and a transmission/reception of the ultrasonic waves having a relatively low frequency, thereby alternately generating the reception frame data which includes the harmonic component and the reception frame data which includes the fundamental wave component. As a result, a plurality of reception frames arranged in a line on the time axis is formed. Each frequency is set by the control unit 24.

The edge-enhanced image generation unit 32 generates the compensation frame data by applying the wavelet fusion method on the plurality of reception frame data (reception frame data of the plurality of fundamental wave components) obtained by transmission/reception of a low-frequency ultrasonic wave as in the first embodiment. The edge-enhanced image generation unit 32 generates the compensation frame data each time the reception frame data is generated. As a result, the plurality of compensation frames arranged in a line on the time axis is formed.

In the fifth embodiment, the basic image generation unit 30 does not perform the processing.

The synthesis unit 34 generates the output frame data by performing weighted averaging of the reception frame data and the compensation frame data of the harmonic component.

The fifth embodiment is applied to a case where a puncture needle is used, for example. This point will be described in detail below.

An example of a scanning surface according to the fifth embodiment is shown in FIG. 10. The scanning surface 94 is a scanning surface formed by transmission/reception of a high-frequency ultrasonic wave, and the scanning surface 96 is a scanning surface formed by transmission/reception of the low-frequency ultrasonic wave. In addition, the puncture needle 98 is inserted into the scanning surfaces 94, 96.

The puncture needle 98 is more likely to be conspicuous in an image which includes a fundamental wave component obtained by the low-frequency ultrasonic wave than an image which includes a harmonic component obtained by the high-frequency ultrasonic wave. The scanning surface 96 is formed by deflecting the ultrasonic beam such that the ultrasonic beam is transmitted and received by the puncture needle 98 from a direction orthogonal to the puncture needle 98 so that the puncture needle 98 is more conspicuous in the image which includes the fundamental wave component.

An example of the reception frame sequence generated by repeating transmission/reception of the high frequency ultrasonic wave and the transmission/reception of the low frequency ultrasonic wave is shown in FIG. 11.

As an example, each reception frame is generated in the order of the reception frames 100, 102a, 102b, 104a, 104b, . . . . The reception frame 100, 102b, 104b are the reception frames which includes the high frequency component obtained by transmission and reception of the high frequency ultrasonic wave. The reception frame 102a and 104a are reception frames which includes the fundamental wave components obtained by transmission/reception of the low-frequency ultrasonic wave.

The edge-enhanced image generation unit 32 generates the compensation frame 106 by applying the wavelet fusion method to the reception frames 102a, 104a, for example. The synthesis unit 34 generates the output frame 108a by performing weighted averaging to the reception frame 102b and the compensation frame 106, and generates the output frame 108b by performing weighted averaging to the reception frame 104b and the compensation frame 106. Thereafter, the edge-enhanced image generation unit 32 generates the compensation frame by applying the wavelet fusion method to the next two reception frames on the time axis, and the synthesis unit 34 generates the output frame by performing weighted averaging to the next reception frame and the compensation frame on the time axis. Thereafter, each time the reception frame is generated, these processes are repeated, so as to form the plurality of output frames arranged in a line on the time axis.

As described above, the edge component of the puncture needle is sharpened by applying the wavelet fusion method for the reception frame which includes the fundamental wave component where the puncture needle is more conspicuous. Since the reception frame which includes the harmonic component is the reception frame where image quality is given priority, the image quality of the tissue in the living body is good, and the ultrasound image (B-mode tomographic image) where the puncture needle is sharpened is obtained by synthesizing the reception frame and the compensation frame which includes the harmonic component thereof.

In the first to fifth embodiments described above, the processing is performed on the two-dimensional reception frame as the object, but the processing may also be performed on the three-dimensional volume data as the object.

REFERENCE SIGN LIST 14 signal processing unit
16 synthesis processing unit
28 memory
30 basic image generation unit
32 edge-enhanced image generation unit
34 synthesis unit

The invention claimed is:

1. An ultrasonic diagnosis device comprising:
a base frame generation unit configured to generate a base frame by synthesizing a frame sequence obtained by transmission/reception of ultrasonic waves;
a compensation frame generation unit configured to generate a compensation frame where an edge component is emphasized based on the frame sequence; and
a synthesis unit configured to generate an output frame by synthesizing the base frame and the compensation frame;
wherein the synthesis unit synthesizes the base frame and the compensation frame by changing a weight in an area unit or a pixel unit in the base frame and the compensation frame;
wherein each frame included in the frame sequence is a frame where deflection angles of ultrasonic waves are different from each other; and
wherein the synthesis unit sets a weight for an area where a number of frames overlapping each other is small to be smaller than a weight for an area where a number of frames overlapping each other is large in the compensation frame.

2. The ultrasonic diagnosis device according to claim 1, wherein
the compensation frame generation unit generates a component image set which includes a plurality of component-specific images by applying wavelet transform to the frame sequence, and generates the compensation frame by synthesizing and inversely converting the plurality of component-specific images.

3. The ultrasonic diagnosis device according to claim 2, wherein
the compensation frame generation unit may apply a maximum value method in the synthesis of the plurality of component-specific images.

4. The ultrasonic diagnosis device according to claim 1, wherein
the synthesis unit synthesizes the base frame and the compensation frame by changing a weight for each type of an ultrasonic probe in the base frame and the compensation frame.

5. The ultrasonic diagnosis device according to claim 1, wherein
each frame included in the frame sequence is a frame where the deflection angles of the ultrasonic waves are equal to each other and obtained at time different from each other.

6. The ultrasonic diagnosis device according to claim 5, wherein
the base frame generation unit generates the base frame based on a part of the frame sequence, and
the compensation frame generation unit generates the compensation frame based on a larger number of frames than a number of frames used when generating the base frame sequence.

7. A non-transitory computer-readable medium storing a program, which causes a computer to function as:
a base frame generation unit configured to generate a base frame by synthesizing a frame sequence obtained by transmission/reception of ultrasonic waves;
a compensation frame generation unit configured to generate a compensation frame where an edge component is emphasized based on the frame sequence; and
a synthesis unit configured to generate an output frame by synthesizing the base frame and the compensation frame;
wherein the synthesis unit synthesizes the base frame and the compensation frame by changing a weight in an area unit or a pixel unit in the base frame and the compensation frame;
wherein each frame included in the frame sequence is a frame where deflection angles of ultrasonic waves are different from each other, and
wherein the synthesis unit sets a weight for an area where a number of frames overlapping each other is small to be smaller than a weight for an area where a number of frames overlapping each other is large in the compensation frame.

* * * * *